(12) United States Patent
Deinzer et al.

(10) Patent No.: US 8,498,692 B2
(45) Date of Patent: Jul. 30, 2013

(54) METHOD FOR DISPLAYING A MEDICAL IMPLANT IN AN IMAGE AND A MEDICAL IMAGING SYSTEM

(75) Inventors: Frank Deinzer, Röthenbach (DE); Thomas Brunner, Nürnberg (DE); Michael Pflaum, Röttenbach (DE)

(73) Assignee: Siemens Aktiengesellschaft, München (DE)

( * ) Notice: Subject to any disclaimer, the term of this patent is extended or adjusted under 35 U.S.C. 154(b) by 1707 days.

(21) Appl. No.: 11/515,303

(22) Filed: Aug. 31, 2006

(65) Prior Publication Data

US 2007/0055131 A1 Mar. 8, 2007

(30) Foreign Application Priority Data

Sep. 1, 2005 (DE) .......................... 10 2005 041 602

(51) Int. Cl.
*A61B 5/05* (2006.01)
(52) U.S. Cl.
USPC ........................................................ 600/427
(58) Field of Classification Search
USPC ........................................................ 600/427
See application file for complete search history.

(56) References Cited

U.S. PATENT DOCUMENTS

| | | | |
|---|---|---|---|
| 6,386,758 B2 | 5/2002 | Loser | |
| 2003/0097068 A1* | 5/2003 | Hossack et al. | 600/443 |
| 2004/0171924 A1* | 9/2004 | Mire et al. | 600/407 |
| 2005/0054895 A1 | 3/2005 | Hoeg et al. | |
| 2005/0075563 A1* | 4/2005 | Sukovic et al. | 600/427 |
| 2005/0113681 A1* | 5/2005 | DeFreitas et al. | 600/426 |

FOREIGN PATENT DOCUMENTS

| | | |
|---|---|---|
| DE | 100 05 628 A1 | 8/2001 |
| EP | 1 504 726 A1 | 2/2005 |
| WO | WO 96/25881 A1 | 8/1996 |
| WO | WO 9625881 A1 * | 8/1996 |
| WO | WO 00/56215 A1 | 9/2000 |
| WO | WO 03/051219 A1 | 6/2003 |

OTHER PUBLICATIONS

Robert A. McLaughlin, John Hipwell, David J. Hawkes, J. Alison Noble, James V. Byrne, Tim Cox; "A Comparison of 2D-3D Intensity-Based Registration and Feature-Based Registration for Neurointerventions"; 2002; MICCAI 2002, LNCS 2489; pp. 517-524; Springer-Verlag; Berlin Heidelberg, Germany.
Graeme P. Penney, Jürgen Weese, John A. Little, Paul Desmedt, Derek L. G. Hill, David J. Hawkes; "A Comparison of Similarity Measures for Use in 2-D-3-D Medical Image Registration"; IEEE Transactions on Medical Imaging; Aug. 1998; pp. 586-595; vol. 17, No. 4.

* cited by examiner

*Primary Examiner* — Tse Chen
*Assistant Examiner* — Hien Nguyen

(57) ABSTRACT

To allow safe treatment of a patient, in particular a puncture or biopsy using a needle, a 2D sectional image of an implant plane and a further 2D sectional image of an orthogonal plane are generated from a 3D image data record of a region to be examined. The two planes are hereby oriented such that the needle is on the one hand located within the implant plane and on the other hand is oriented in a perpendicular manner in respect of the orthogonal plane. The parallel display of the 2D images allows the doctor to acquire the relative position of the needle in relation to the region to be examined in a simple and intuitive manner.

18 Claims, 4 Drawing Sheets

METHOD FOR DISPLAYING A MEDICAL IMPLANT IN AN IMAGE AND A MEDICAL IMAGING SYSTEM

CROSS REFERENCE TO RELATED APPLICATIONS

This application claims priority of German application No. 10 2005 041 602.0 filed Sep. 1, 2005, which is incorporated by reference herein in its entirety.

FIELD OF THE INVENTION

The invention relates to a method for displaying a medical implant extending in the direction of insertion, in particular a treatment device, e.g. a needle, in a medical image of a region to be examined. The invention further relates to a medical imaging system for implementing said method.

BACKGROUND OF THE INVENTION

During the medical treatment of a patient, for example during the treatment of tumors, aneurysms and stenoses, a medical treatment device, for example a needle, is inserted into the body and guided to the diseased point in the body. This is then treated for example by puncture or biopsy. In the case of certain organs, for example the spleen, gallbladder, bowel or spinal cord, the medical treatment device, referred to here generally as an implant, has to be guided very precisely to avoid damaging the organ to be treated or adjacent organs.

The doctor can monitor the guiding of the implant within the body in a parallel manner via imaging systems. One problem here is displaying the location of the medical implant within the body in such a manner for medical personnel that the actual position, in particular the relative position of the implant in relation to the individual organs, can be acquired as intuitively as possible by the personnel providing the treatment.

The imaging method used to display the region to be examined generally involves reconstructing 3D image data records from the measurement data of an angiography, computed tomography (CT) or magnetic resonance (MR) system and reproducing them as required as a three-dimensional image of the region to be examined. The systems listed here therefore supply image volume data relating to the region to be examined. Contrast agents are frequently injected to improve the display.

The current position of the implant is generally superimposed in the images thus reconstructed. To this end the actual position of the implant is acquired for example via location sensors attached to the implant. The location coordinates of the implant thus acquired are then correlated with the coordinates of the image data record, to ensure that the display in the image corresponds to actual circumstances. With such a visualization of the implant in a three-dimensional image, it is however often difficult for the personnel providing the treatment to orient themselves, due to the complexity of the individual organs. It is particularly difficult for medical personal to identify how the implant will progress further.

As an alternative to visualizing the implant in a 3D image, it is also possible to visualize it in a two-dimensional image display, for example what is known as multiplanar reconstruction of the 3D data record. However intuitive acquisition of the relationship between the implant and the tissue being passed through is difficult here too.

Further options for orientation when guiding the implant involve showing up individual vessels using fluoroscopy, e.g. by means of contrast agents, to obtain orientation points or carrying out image reconstruction at short intervals, in particular what is known as 3D angio-reconstruction, to be able to establish the location of the implant in each instance. Finally doctors can simply rely on their anatomical knowledge and insert the implant more or less blindly into the body during fluoroscopic examination of the region to be examined, until it reaches the required point.

SUMMARY OF THE INVENTION

The object of the invention is to allow the most intuitive visual acquisition possible of the implant, in particular a treatment device such as a needle, during medical treatment.

The object is achieved according to the invention by a method with the features of the first independent claim. According to this, provision is made for the medical implant, e.g. a needle, to be displayed in an image of a region to be examined. The region to be examined is represented by a 3D image data record. The coordinates of the implant are correlated with those of the 3D data image record, such that the relative positions of the implant and the region to be examined are also correctly reproduced in the image display. To allow intuitive acquisition, there is provision for the generation of a 2D sectional image of an orthogonal plane and a further 2D sectional image of an implant plane from the 3D image data record. The orthogonal plane is hereby oriented in a perpendicular manner to the insertion direction or the longitudinal direction of the implant. In contrast the implant plane extends in the direction of insertion. The implant plane and the orthogonal plane are therefore perpendicular to each other. The location of the implant is thereby displayed in each instance in the 2D sectional images. The full length of the implant therefore appears in the 2D sectional image of the implant plane, hereafter abbreviated to the "in-plane image", while in contrast in the 2D sectional image of the orthogonal plane, hereafter abbreviated to the "orthogonal image", the implant just appears generally as a point or circular object.

Intuitive acquisition of the position of the implant and in particular its orientation in relation to the region to be examined is hereby achieved in particular due to the two-dimensionality, as experience has proven that orientation is significantly simpler in a two-dimensional plane. Visualizing the implant in two planes oriented orthogonally in relation to each other means that the three-dimensional information about the location of the implant is obtained at the same time and can easily be acquired. Dividing it into two two-dimensional images allows the future path of the implant to be identified. This can be seen in particular from the "in-plane image". It is thus easy for medical personnel to identify which tissue regions the needle has already penetrated and which tissue regions the needle will encounter next.

According to one expedient development, the extension or projection of the implant in the longitudinal and therefore the insertion direction is displayed. This additional display allows to doctor to identify immediately which path the needle is taking and which tissue will be penetrated by the needle tip.

According to one expedient development the implant plane can also be rotated about the insertion direction, such that in-plane images can be displayed as required in different rotational positions about the insertion direction. By rotating the implant plane, it is possible to obtain a three-dimensional impression of the tissue surrounding the needle within the in-plane display. It can thus be determined readily in this manner how near the needle tip is to an adjacent organ. The rotational position of the implant plane about the insertion direction is hereby preferably selected such that the distance from an adjacent critical organ or tissue as small as possible.

In one expedient development the distance between the orthogonal plane and the needle tip can be varied for displaying in the orthogonal image. In the display of the current needle position the orthogonal plane runs precisely through the needle tip. In other words the needle tip, which is seen as a point or circular shape, shows the precise position. The variable nature of the distance between the orthogonal plane and the needle tip also means that it is possible to project the future path of the needle tip in the orthogonal image. In other words the needle tip is also expediently projected along the insertion direction into the distant plane in the orthogonal image of an orthogonal plane at a distance from the needle tip. This measure also means that medical personnel are able in particular to acquire the future path of the needle tip easily and intuitively.

The actual distance is hereby preferably indicated directly in the orthogonal image.

For the most user-friendly operation possible for the doctor, the location of the orthogonal plane and/or the implant plane, i.e. in particular the rotation of the implant plane about the insertion direction or the translation of the orthogonal plane in the insertion direction, can be adjusted using an operating element. In other words the doctor is able to define the location of the orthogonal plane and/or the implant plane and change it during the examination, such that it is possible to select the most favorable display in each instance.

According to one expedient development the orthogonal image and the in-plane image are hereby displayed simultaneously and in parallel next to each other. In this expedient embodiment the doctor therefore does not have to switch between the two images. Instead the doctor can look at both views in a parallel manner. The images are hereby preferably displayed on separate screens or at least separate screen areas.

To assist further with orientation, a 3D image obtained from the 3D image data record and/or a fluoroscopy image is/are also displayed. A fluoroscopy image in general terms is an image that can be derived directly from the measurement data of the medical imaging device without image reconstruction. When an x-ray computed tomograph is used, this fluoroscopy image corresponds to a regular x-ray image. When displaying the 3D image, it is expedient for the implant plane and/or the orthogonal plane as well as the implant also to be displayed in the 3D image, such that it is also simple for the doctor to acquire the location and position of the needle within the three-dimensional display.

The displayed images are hereby expediently adjusted in real time, if the needle and/or region to be examined changes location. If the doctor moves the needle, this movement in particular is acquired by position sensors and the display in the image is adjusted correspondingly. Movement of the region to be examined, for example due to movement of the patient, is achieved by ongoing image reconstruction in particular, in particular with the aid of what are known as 2D/3D fusion methods. The change in the location of the patient can alternatively also be brought about by adjusting the patient support table holding the patient. In this instance the changed position data is alternatively or additionally transmitted to in an expedient manner directly from the patient support table to the medical imaging system and taken into account arithmetically there.

When the needle or region to be examined changes location, the location change is preferably acquired in each instance in relation to a fixed spatial coordinates system, with the relative locations of the needle and the displayed region to be examined being calculated from this. In general provision is therefore expediently made for both the coordinates of the 3D image data record and those of the implant to be established in relation to the spatial coordinates system, such that the relative location of the implant is implicitly defined in relation to the region to be examined.

According to the invention the object is also achieved by a medical imaging system with the features of the second independent claim. The advantages and preferred embodiments cited in relation to the method should also be applied in a similar manner to the medical imaging system.

BRIEF DESCRIPTION OF THE DRAWINGS

An exemplary embodiment of the invention is described in more detail below with reference to the figures, each of which shows schematic and in some instances highly simplified displays, in which.

Parts with identical action are shown with the same reference characters in the figures.

DETAILED DESCRIPTION OF THE INVENTION

Figure 1:
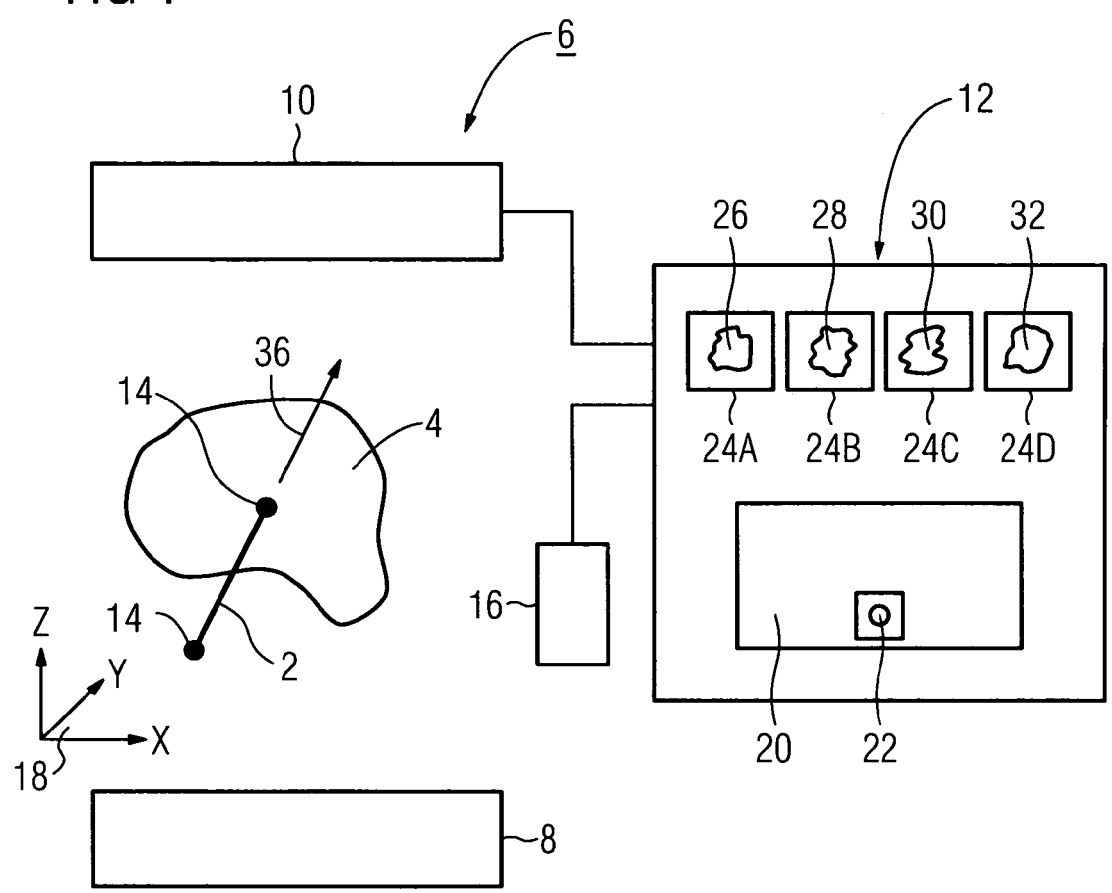
FIG. 1 shows a block diagram of a medical imaging system.

The medical imaging system shown in a highly simplified manner in FIG. 1 is used to assist during the medical treatment of a patient. It is used in particular to visualize the position of a treatment device, in particular a needle 2, in relation to a region 4 to be examined, in a manner that can be acquired intuitively by medical personnel. In the exemplary embodiment the medical imaging system comprises a medical imaging examination device 6, for example a C-arm computed tomography device, a magnetic resonance device or even an angiography system. The examination device 6 has a radiation source 8 and a detector 10. The radiation source 8 is in particular an x-ray radiation source and the detector 10 is an x-ray detector. The radiation source 8 and detector 10 are disposed opposite each other. The patient with the region 4 to be examined is located between them. The measurement data acquired by the detector 10 is transmitted as raw image data to an image-processing system 12. Known methods are used in this to prepare, reconstruct and display images of the region 4 to be examined.

The medical imaging system is also configured to acquire the position of the needle 2. To this end, position sensors 14 and an associated receiver 16 are provided on the needle to acquire position signals, which are emitted by the position sensors 14. The position of the needle 2 is acquired in relation to a fixed spatial coordinates system 18. The location of the region 4 to be examined is similarly specified in relation to the fixed spatial coordinates system 18.

The image-processing system 12 also comprises an operating console 20 with an operating element 22, for example configured as a joystick. A number of display elements 24A, 24B, 24C, 24D, in particular separate monitors, are also provided. Both the operating console 20 and the display elements 24A, 24B, 24C, 24D can be configured as separate units or can be integrated within a common device, as shown in FIG. 1.

The raw image data supplied by the detector 10 is processed within the image-processing system 12. A fluoroscopy image 26 generated from the raw data is preferably displayed on the display element 24A, an in-plane image 28 on the display element 24B, an orthogonal image 30 on the display element 24C and a 3D image 32 on the display element 24D. The in-plane image 28 here corresponds to the image shown in FIG. 2D, the orthogonal image 30 to the image shown in FIG. 3D and the 3D image corresponds in particular to the image shown in FIG. 4.

A 3D image data record is generated from the raw image data obtained with the aid of methods that are known per se in the image-processing system 12. This 3D image data record therefore represents the region 4 to be examined, i.e. the information to be assigned to the region 4 to be examined is contained in the 3D image data record.

Figure 2A:
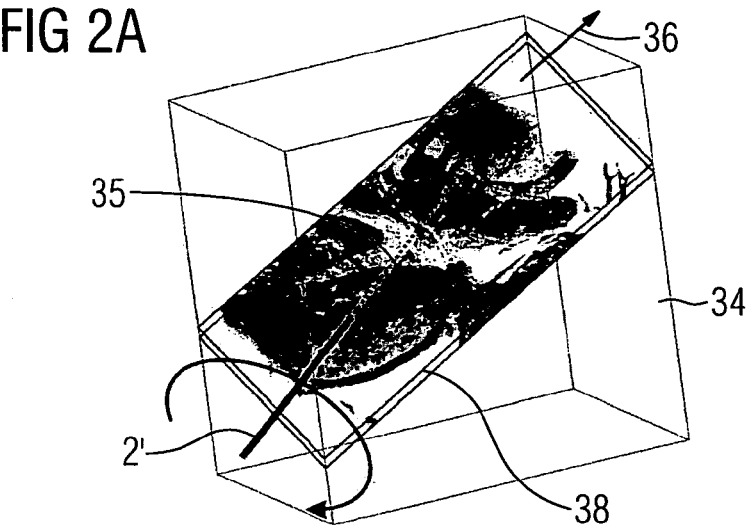
FIG. 2A shows the display of an implant plane within a 3D volume of a 3D image data record together with a needle and the projection of the future path of the needle.
Figure 2B:
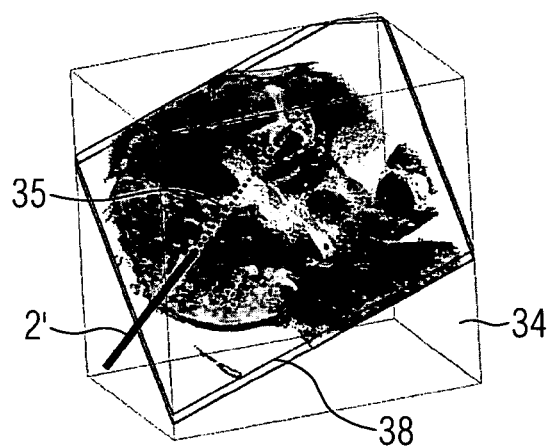
FIGS. 2B, 2C show displays of two further implant planes within the 3D volume according to FIG. 2A, with the implant planes being rotated about the insertion direction defined by the longitudinal axis of the implant.
Figure 2C:
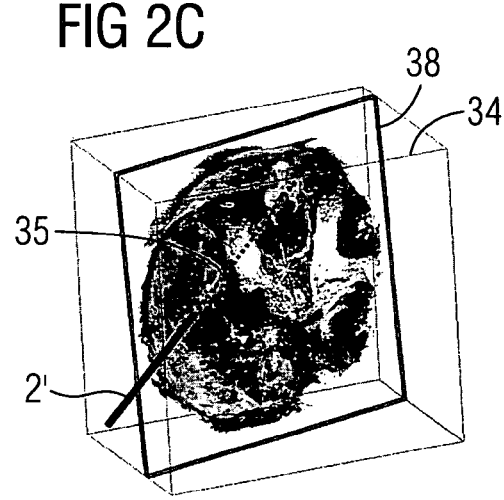
Figure 3A:
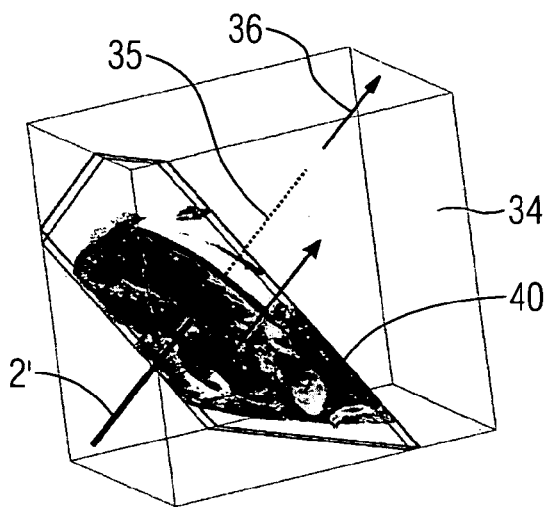
FIG. 3A shows the display of an orthogonal plane within the 3D volume together with the implant, the orthogonal plane running through the tip of the implant.
Figure 3B:
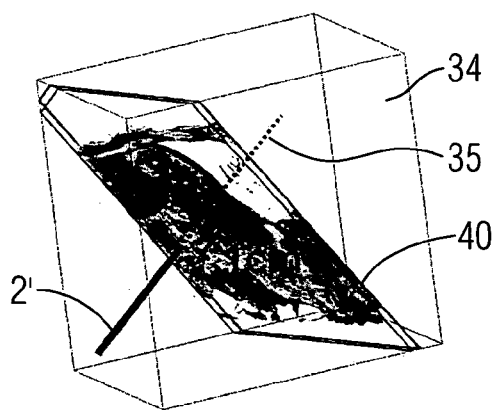
FIGS. 3B, 3C show further displays of an orthogonal plane within the 3D volume at a different distance from the tip of the implant.
Figure 3C:
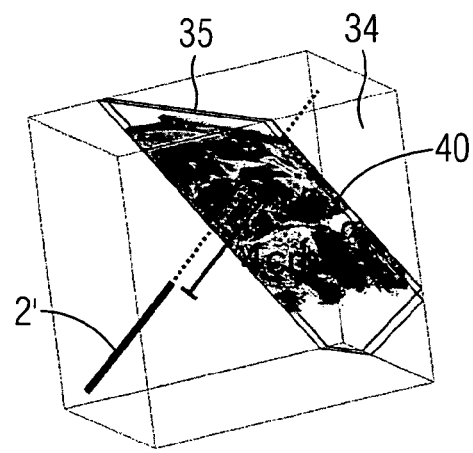
Figure 3D:
FIG. 3D shows an orthogonal image obtained for the sectional image according to FIG. 3C.
Figure 4:
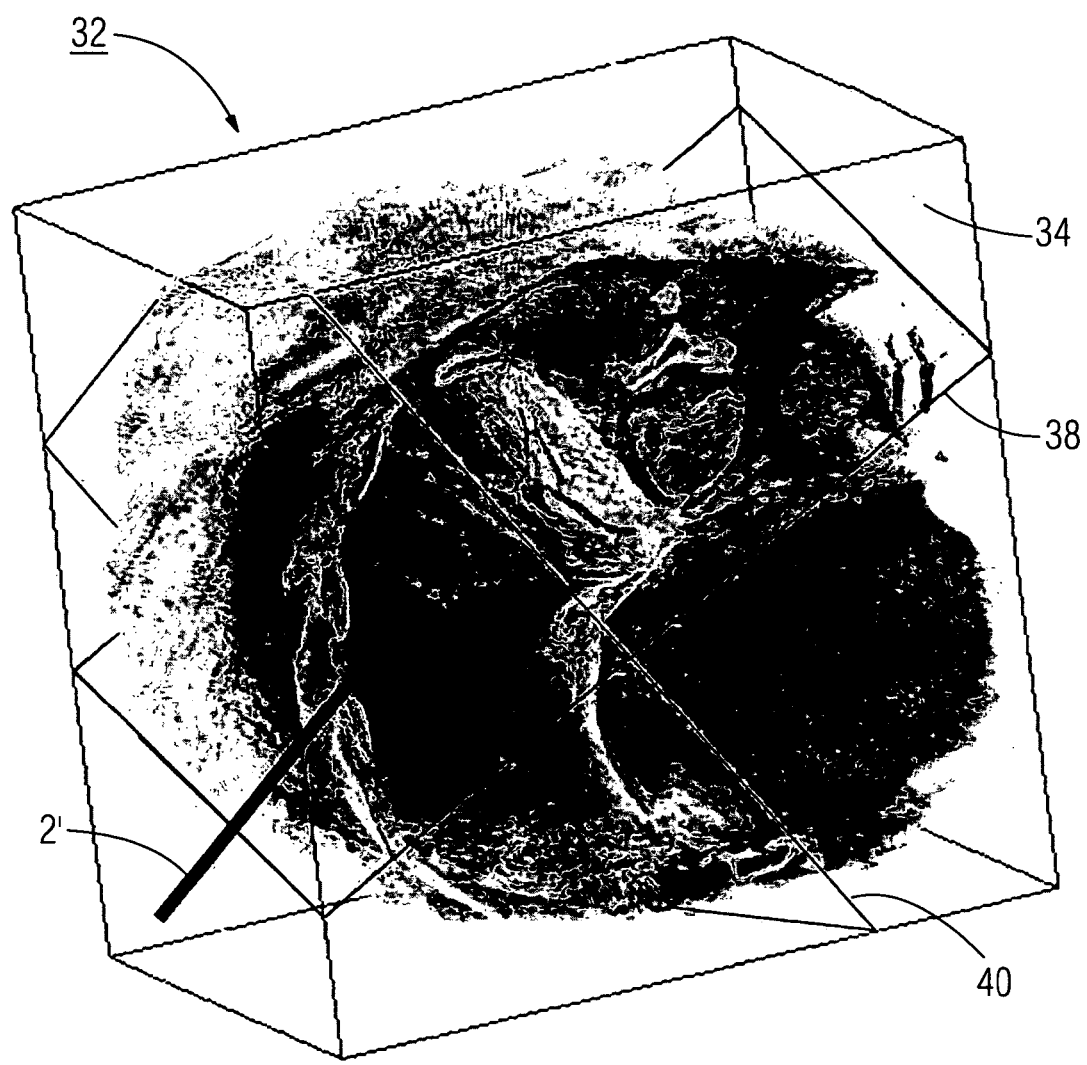
FIG. 4 shows a 3D image of the three-dimensional data record in the 3D volume with the orthogonal and implant planes shown and with the implant displayed.

FIGS. 2 to 4 show a cuboid 3D volume 34, which reproduces the spatial boundaries. To assist medical personnel and in particular to help with orientation in respect of the location of the needle 2, provision is made for an in-plane image 28 and preferably parallel to this an orthogonal image 30 to be created from the 3D image data record, each displaying the current position of the needle 2 or the projected position (projection 35). The displayed image of the needle 2 in FIGS. 2 to 4 is marked with the reference character 2'.

To generate these images 28, 30 and the image 32, the coordinates of the needle 2 have to be correlated with those of the 3D image data record. In the exemplary embodiment provision is made on the one hand for the spatial coordinates of the needle 2 to be determined within the spatial coordinates system 18 with the aid of the position sensors 14 and the receiver 16. Parallel to this, the spatial coordinates of the 3D image data record are also determined in the spatial coordinates system 18. The coordinates of the needle 2 and the 3D image data record are therefore correlated with each other using the fixed spatial coordinates system 18, such that the relative position of the needle 2 in relation to the region 4 to be examined can be reliably displayed in each instance in the images 28 to 32.

To generate the images 28, 30, the location of the needle 2 and in particular its longitudinal and thus its insertion direction 36 are first determined. To generate the in-plane image 28, a sectional plane is established through the 3D image data record, hereafter referred to as the implant plane 38 (see also FIGS. 2A, 2B, 2C). The insertion direction 36 is hereby within the implant plane 38, i.e. the insertion direction 36 is one of the two directions spanning the implant plane 38. A two-dimensional sectional image, namely the in-plane image 28, is created and displayed from the data in the implant plane 38.

In contrast, to generate the orthogonal image 30, a sectional plane referred to as the orthogonal plane 40 is provided, which is oriented perpendicular to the insertion direction 36 (see also FIGS. 3A, 3B, 3C). The orthogonal plane 40 and the implant plane 38 are therefore perpendicular to each other.

The orthogonal image 30 is also created and displayed from the 3D image data within the orthogonal plane 40 here.

Figure 2D:
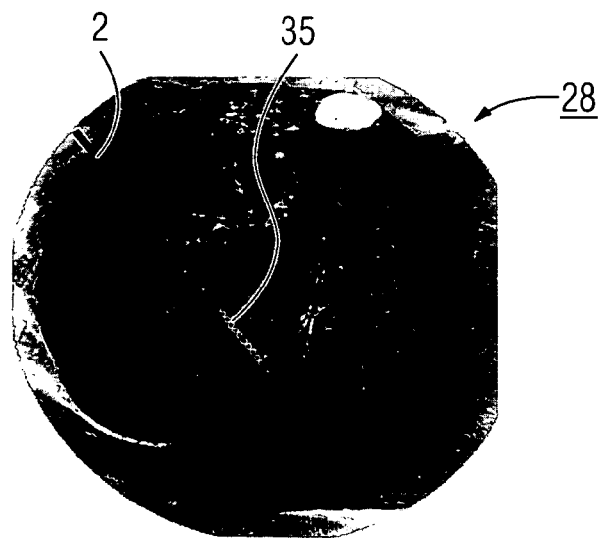
FIG. 2D shows an in-plane image obtained for the sectional image according to FIG. 2C.

As shown in FIGS. 2D, 3D, the projection 35 of the future, forecast path route is superimposed in the images 28, 30 in addition to the needle 2. The doctor providing the treatment can thus readily identify which tissue the needle 2 has to penetrate, if the current direction is maintained.

To provide the doctor with the best possible orientation, it is possible to change the in-plane image 28 by rotating the implant plane 38 about the insertion direction 36, as shown in FIG. 2A by the double arrow. Rotating the implant plane 38 allows different sectional planes to be defined through the 3D image data record, such that different in-plane images 28 are obtained. By rotating the implant plane 38, the doctor is therefore able to display the tissue disposed around the needle 2. The implant plane is hereby rotated using the operating element 22.

The operating element 22 similarly allows the orthogonal plane 40 to be varied in the insertion direction 36, as shown by the double arrow in FIG. 3A. It is therefore possible to position the orthogonal sectional plane at different distances from the needle tip, as shown by the distance bars in FIGS. 3B and 3C. The projected position of the needle 2 (projection 35) is also displayed in the orthogonal images 30 obtained from these orthogonal planes 40 such that the doctor is also able to identify the position the needle will reach within the tissue here. At the same time—as shown in FIG. 3D—the actual distance between the needle tip and the projection 35 of the needle tip displayed in the image and thus the distance between the needle tip and the orthogonal plane 40 is shown and superimposed.

The doctor can therefore use the images 26 to 32 to monitor the insertion process and progress of the path of the needle 2 in a very precise and intuitive manner. The position of the needle 2' or the projection 35 shown in the images 28 to 32 is continuously updated, such that a real-time display is achieved. To this end the actual coordinates of the needle 2 are continuously acquired. If the patient does not move and is in a sufficiently fixed position, the position of the region 4 to be examined remains unchanged, such that it would be adequate in principle to create a 3D image data record at the start of the treatment. Current 3D image data records are preferably obtained in a manner known per se continuously or at short intervals during treatment, in particular during critical treatments entailing a high risk of damage to sensitive organs. This ensures that the relative position of the needle 2 in relation to the region 4 to be examined, as displayed in the images 28 to 32, also corresponds to actual circumstances.

To clarify the orientation and location of the needle 2 and to assist more with orientation, the individual images 28 to 32 are suitably shaded or colored. Also—as shown in FIG. 4—the orthogonal plane 40 and the implant plane 38 are displayed in the 3D image 32.

The method described here provides assistance with visualization when inserting the needle 2 into the patient, allowing acquisition of the actual relative position of the needle 2 in relation to the region 4 to be examined in a manner that is intuitive for the doctor and in particular can be carried out in real time. By providing limited degrees of freedom, specifically rotation in relation to the insertion direction 36 and translation along the insertion direction 36 for the implant plane 38 or the orthogonal plane 40, this method also allows an interactive display, in other words doctors themselves can easily select the best display. Generally the method described here increases operation safety and reduces the risk of damage to adjacent, sensitive tissue areas or organs during the intervention.

The invention claimed is:

1. A method for displaying in images position, orientation and direction of insertion of a medical implant while undertaking a process of translating the medical implant along an insertion direction and through tissue in a patient's body to a point in the body, the images providing views of an examination region of the patient derived from a 3D image data record, the method comprising:
   continually updating 3D image data records with a C-arm computed tomography imaging system of the type having an x-ray radiation source and an x-ray detector positionable about a patient;
   generating from the 3D image data records 2D sectional images of one or more implant planes along an insertion direction of the implant;
   generating from the 3D image data records 2D sectional images perpendicular to the implant planes;
   providing at least two position sensors on the implant which emit position signals;
   using the signals from the at least two position sensors to determine coordinates and insertion direction of the implant, during the process of translating the medical implant to a point in the body, based on the coordinates of the 3D image data records; and
   displaying in one or more of the 2D section images: position, orientation and direction of insertion of a medical implant during the process of translating the medical implant along an insertion direction and to the point in the body, thereby enabling via one or more images an identification of tissue regions already traversed by the medical implant and a tissue region yet to be traversed but the medical implant.

2. The method as claimed in claim 1, wherein the extension of the implant is displayed in the insertion direction.

3. The method as claimed in claim 1, wherein the implant plane is rotated about the insertion direction so that a plurality of sectional images is displayed at a plurality of rotational positions.

4. The method as claimed in claim 3, wherein the rotational positions are selected substantially close to an adjacent organ or tissue of the patient.

5. The method as claimed in claim 1, wherein the orthogonal plane moves a distance with respect to the location of the implant along the insertion direction.

6. The method as claimed in claim 5, wherein the distance is displayed.

7. The method as claimed in claim 1, wherein the sectional images of the implant plane and the orthogonal plane are displayed simultaneously.

8. The method as claimed in claim 7, wherein a 3D image of the examination region generated from the 3D image data record is displayed simultaneously with one or more of the 2D images.

9. The method as claimed in claim 8, wherein the implant plane or the orthogonal plane is displayed within the 3D image.

10. The method as claimed in claim 1, wherein a fluoroscopy image of the examination region is displayed.

11. The method as claimed in claim 1, wherein the display of the implant in the sectional images is adjusted in real time if the location of the implant or the examination region is changed.

12. The method as claimed in claim 1, wherein the coordinates of the 3D image data record and of the implant are determined in a fixed spatial coordinate system.

13. The method as claimed in claim 1, wherein the medical implant is a medical treatment device.

14. The method as claimed in claim 13, wherein the medical treatment device is a needle.

15. A medical imaging system which determines and displays position, orientation and direct of insertion of a medical implant during a process of translating the medical implant along an insertion direction and through tissue in a patient's body to a point in the body, comprising:
   a C-arm computed tomography imaging system of the type having an x-ray radiation source and an x-ray detector positionable about a patient configured to generate an image of an examination region of the patient, the image displaying a medical implant extending in an insertion direction; and
   an image-processing system which:
      reconstructs a 3D image record based on 2D data records of the image,
      correlates a coordinate of the 3D image data record with a coordinate of the implant based multiple position sensors, located on the implant, of the type which emit position signals,
      generates a 2D sectional image of an implant plane along an insertion direction of the implant and a 2D sectional image along a plane orthogonal to the implant plane from the 3D image data record, and
      displays location, orientation and direction of insertion of the implant in one or more of the 2D sectional images during the process of translating the medical implant along an insertion direction, through the tissue and to the point in the body.

16. The method of claim 1 wherein the step of displaying position, orientation and direction of insertion includes simultaneously displaying both a sectional image of an implant plane and a sectional image perpendicular to the implant plane and a location of the implant in the sectional images.

17. The method of claim 1 wherein displaying position, orientation and direction of insertion of the medical implant illustrates a tissue region which the medical device has traversed and a tissue region toward which the medical device is oriented to traverse upon further insertion.

18. The method of claim 1 further including changing one or more of the 2D sectional images to view position, orientation or direction of insertion of the medical implant with a joystick.

* * * * *